(12) United States Patent
Woodard et al.

(10) Patent No.: US 7,231,832 B2
(45) Date of Patent: Jun. 19, 2007

(54) SYSTEM AND METHOD FOR DETECTING CRACKS AND THEIR LOCATION

(75) Inventors: Stanley E. Woodard, Hampton, VA (US); Qamar A. Shams, Yorktown, VA (US)

(73) Assignee: United States of America as represented by the Administrator of the National Aeronautics and Space Administration, Washington, DC (US)

( * ) Notice: Subject to any disclaimer, the term of this patent is extended or adjusted under 35 U.S.C. 154(b) by 81 days.

(21) Appl. No.: 11/229,439

(22) Filed: Sep. 12, 2005

(65) Prior Publication Data

US 2006/0070450 A1    Apr. 6, 2006

Related U.S. Application Data

(60) Provisional application No. 60/611,170, filed on Sep. 13, 2004.

(51) Int. Cl.
*G01N 19/08*   (2006.01)
*G01B 7/16*    (2006.01)

(52) U.S. Cl. ............................. 73/799; 73/779

(58) Field of Classification Search ................... 73/799
See application file for complete search history.

(56) References Cited

U.S. PATENT DOCUMENTS 3,918,299 A * 11/1975 Donnadieu .................... 73/772
4,579,004 A *  4/1986 Kalthoff et al. ............... 73/799
7,082,833 B2 *  8/2006 Heyman et al. ............... 73/598

* cited by examiner

*Primary Examiner*—Max Noori
(74) *Attorney, Agent, or Firm*—Robin W. Edwards

(57) ABSTRACT

A system and method are provided for detecting cracks and their location in a structure. A circuit coupled to a structure has capacitive strain sensors coupled sequentially and in parallel to one another. When excited by a variable magnetic field, the circuit has a resonant frequency that is different for unstained and strained states. In terms of strained states, the resonant frequency is indicative of a region of the circuit that is experiencing strain induced by strain in a region of the structure in proximity to the region of the circuit. An inductor is electrically coupled to one end of each circuit. A magnetic field response recorder wirelessly transmits the variable magnetic field to the inductor and senses the resonant frequency of the circuit so-excited by the variable magnetic field.

31 Claims, 4 Drawing Sheets

SYSTEM AND METHOD FOR DETECTING CRACKS AND THEIR LOCATION

Pursuant to 35 U.S.C. §119, the benefit of priority from provisional application 60/611,170, with a filing date of Sep. 13, 2004, is claimed for this non-provisional application.

ORIGIN OF THE INVENTION

The invention was made in part by an employee of the United States Government and may be manufactured and used by or for the Government of the United States of America for governmental purposes without the payment of any royalties thereon or therefore.

BACKGROUND OF THE INVENTION

1. Field of the Invention

This invention relates to crack detection in structures. More specifically, the invention is a system and method for detecting cracks and their location in materials/structures.

2. Description of the Related Art

The detection of cracks and the location thereof in materials/structures is an extremely useful tool in the prediction and prevention of material/structure catastrophes. Ideally, a crack determination system should be capable of constant or on-demand monitoring without affecting the material's/structure's intended purpose. However, there are currently no in-situ crack detection systems or methodologies that can achieve these goals.

SUMMARY OF THE INVENTION

Accordingly, it is an object of the present invention to provide a system and method for detecting cracks and their location in a structure.

Another object of the present invention is to provide a system and method of in-situ crack determination that does not affect the material or structure to which it is coupled.

Another object of the present invention is to provide a system and method for determining if material has been torn or damaged.

Other objects and advantages of the present invention will become more obvious hereinafter in the specification and drawings.

In accordance with the present invention, a system and method are provided for detecting cracks and their location in a structure. At least one circuit is coupled to a structure where each such circuit has a plurality of capacitive strain sensors coupled sequentially and in parallel to one another and in parallel to at least one inductor. When excited by a variable magnetic field, the circuit has a resonant frequency that is (i) a first resonant frequency when the circuit is in an unstrained state, (ii) one of a plurality of second resonant frequencies when the circuit is in a strained state, (iii) a third resonant frequency when the circuit has been broken and the remaining active circuit is in an unstrained state that is substantially different in frequency from the first resonant frequency, and (iv) one of a plurality of fourth resonant frequencies when the circuit is broken and the remaining active circuit is in a strained state that are substantially different in frequency than the plurality of second frequencies when at least a portion of the circuit is strained but not broken. A magnetic field response recorder wirelessly transmits the variable magnetic field to the inductor and senses the resonant frequency of the circuit so-excited by the variable magnetic field.

DETAILED DESCRIPTION OF THE INVENTION

Figure 1:
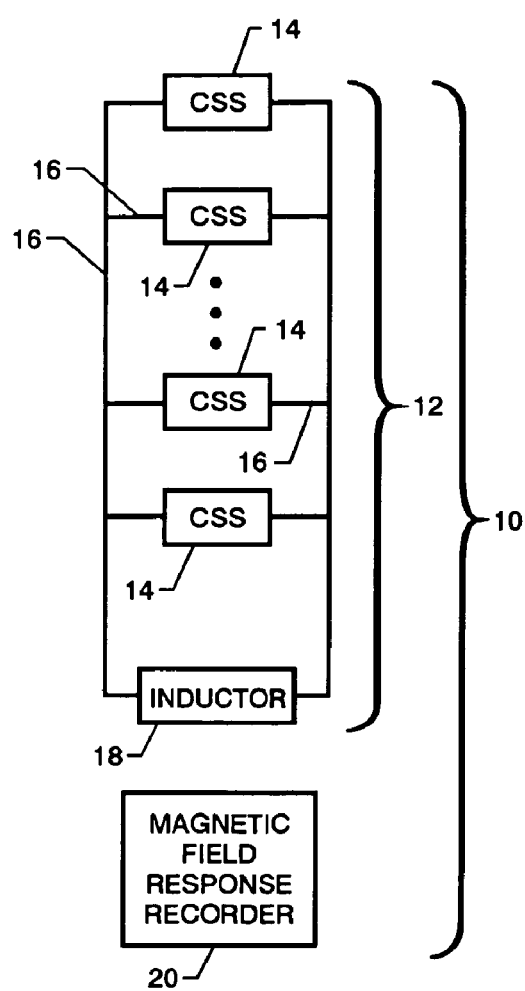
FIG. 1 is a schematic view of a system for detecting cracks in a structure in accordance with the present invention.

Referring now to the drawings, and more particularly to FIG. 1, a system for monitoring strain in a structure in order to detect cracks and their location in the structure is shown and is referenced generally by numeral 10. As will be explained further herein, system 10 can be placed in-situ on and/or in a wide variety of structures to include static structures, mobile vehicle structures, structures made from previously-cured homogenous or multi-layer materials, and homogenous or multi-layer structures that are in a curing phase. Accordingly, it is to be understood that any reference made herein to particular types of structures is done so for purposes of illustration and not limitation.

Figure 2:
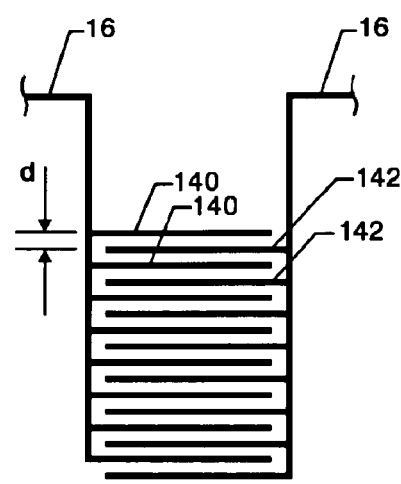
FIG. 2 is an isolated, enlarged view of a capacitive strain sensor used in the present invention.

Crack detection and location system 10 uses a circuit arrangement 12 of capacitive strain sensors ("CSS") 14 electrically coupled in parallel to an inductor 18 (e.g., a spiral inductor) at one end of circuit arrangement 12 and a magnetic field response recorder 20 capable of inductive coupling to inductor 18. More specifically, circuit arrangement 12 is defined by a plurality of CSS 14 that are coupled in sequence to one another in an electrically parallel fashion by electrical leads 16. Each CSS 14 can be constructed from interdigitated electrodes 140/142 as illustrated in FIG. 2 where a separation distance "d" is defined between any two electrodes 140 and 142. The separation distance d affects the capacitance of CSS 14 so that changes in d causes capacitance changes in CSS 14. The separation distance d is affected by any strain that the surface, to which any CSS 14 is affixed, experiences. If circuit 12 is resonating, the resonant frequency thereof is dependent on the capacitance of CSS 14. Accordingly, changes in the capacitance of CSS 14 produce an attendant change in the resonant frequency of circuit 12.

The present invention utilizes the above-described "capacitance-to-resonant frequency" relationship to provide a method and system for crack detection and location as follows. Circuit arrangement 12 is coupled to a structure to be monitored such that circuit arrangement 12 has minimal structural integrity (i.e., the circuit strains/breaks in correspondence with the structure to which it is coupled). Circuit arrangement 12 could be realized through a variety of thin-film fabrication techniques to include deposition directly on an electrically non-conductive structure or on a thin-film insulating substrate that is coupled to an electrically conductive structure.

Once circuit arrangement 12 is in place on a structure, the circuit is excited to resonance by application of a variable magnetic field (e.g., a broadband time-varying magnetic field or a single harmonic magnetic field). If circuit arrangement 12 is not experiencing any strain (because the structure to which it is coupled is not cracking or breaking), circuit arrangement 12 will have a resonant frequency attributable to the capacitance of each unstrained CSS 14. However, if strain develops in the structure beneath one of CSS 14 (hereinafter referred to as the "affected CSS 14"), the strain will impose a corresponding strain on the affected CSS 14. If the strain is sufficient, it can affect the separation distance d (FIG. 2) between interdigitated electrodes of the affected CSS 14 and the circuit arrangement 12 will have a resonant frequency attributable to the capacitance of each strained CSS 14. If the strain experienced by the structure is sufficient to cause a crack therein, the crack will typically cause a break in the affected CSS 14 or the lead lines 16 coupled thereto and/or to successive outboard ones of CSS 14. In either case, the resonant frequency of circuit arrangement 12 will be changed irreversibly relative to the resonant frequency indicative of the unbroken states (strained and unstrained) of circuit arrangement 12. The new resonant frequency is indicative of a location (region) of circuit arrangement 12 that experienced the break. That is, a particular design of circuit arrangement 12 is calibrated so that a strain/break at each CSS 14 creates a unique and known corresponding resonant frequency of circuit arrangement 12. Thus, by monitoring the resonant frequency of circuit arrangement 12 coupled to a structure, one can detect a crack as well as the approximate location thereof in/on the structure.

The application of the variable magnetic field to circuit arrangement 12 and reading of the induced resonant frequency thereof is accomplished by inductively coupling magnetic field response recorder 20 to inductor 18. The operating principles and construction details of recorder 20 are provided in U.S. patent application Ser. No. 10/839,445, the contents of which are hereby incorporated by reference. Briefly, magnetic field response recorder 20 generates and wirelessly transmits a variable magnetic field that is inductively coupled to inductor 18. A current is induced in circuit 12 as a result of Faraday induction. As a result of the induced current, a harmonic magnetic field is produced in inductor 18. The magnetic field frequency in inductor 18 is that of the resonant frequency of circuit 12. The resonant frequency of the entirety of circuit arrangement 12 is thus "read" by recorder 20. Thus, a strain or break in a particular location or region along circuit arrangement 12 produces a unique resonant frequency. When a break occurs, the frequency is indicative of the location/region that experienced the break.

Figure 3:
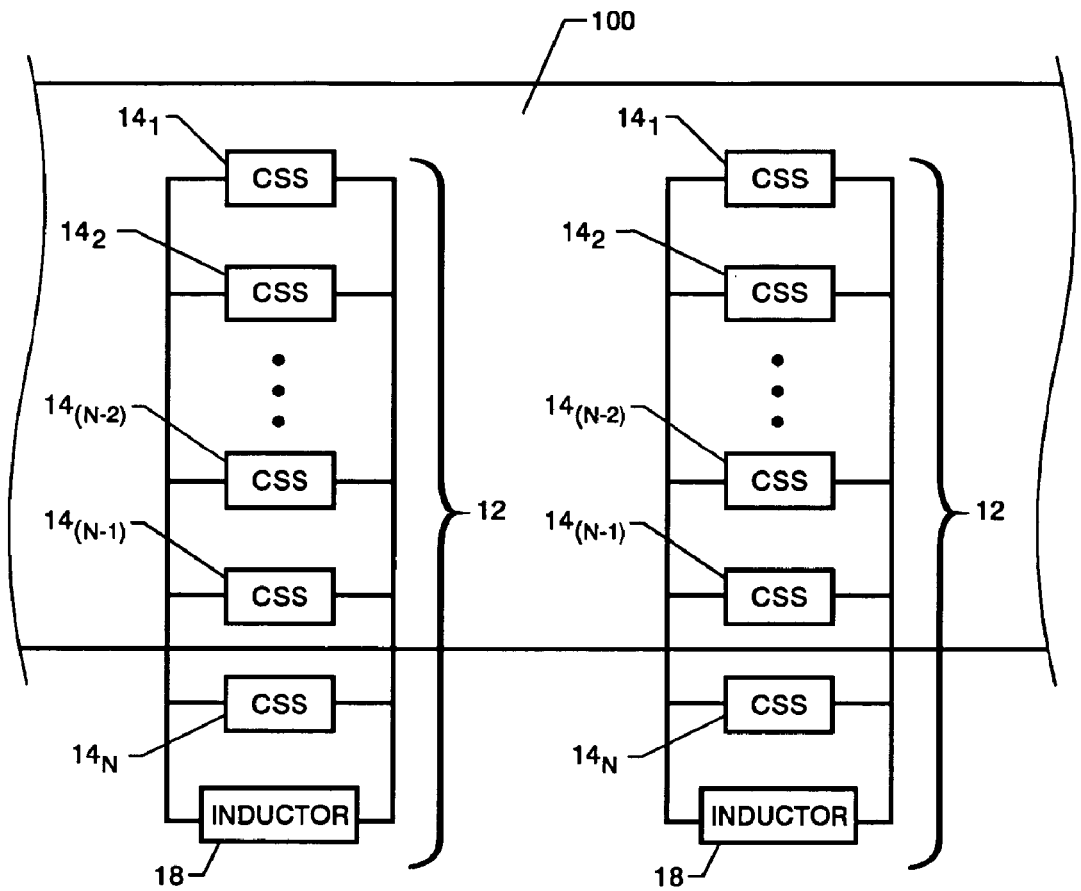
FIG. 3 is a plan view of a structure having crack-sensing circuits coupled to a surface thereof in accordance with an embodiment of the present invention.

As mentioned above, the present invention can be adapted to work in a wide variety of applications. By way of example, a few applications and embodiments will be described herein. Referring first to FIG. 3, two of circuit arrangements 12 are shown coupled to an exterior surface 100 of an existing structure. In this embodiment, each of circuit arrangements 12 has a total of N CSS 14 with CSS $14_1$ through CSS $14_{(N-1)}$ being coupled to surface 100 and CSS $14_N$ remaining uncoupled from surface 100. By keeping the inboard CSS 14 (i.e., CSS $14_N$) uncoupled from surface 100, circuit arrangement 12 will always yield a resonant frequency response regardless of where the structure cracks. To simplify the drawing, it is assumed that surface 100 is electrically non-conductive so that circuit arrangement 12 is simply deposited directly on surface 100. Circuit arrangements 12 can be positioned anywhere on surface 100 in any desired orientation.

Figure 4:
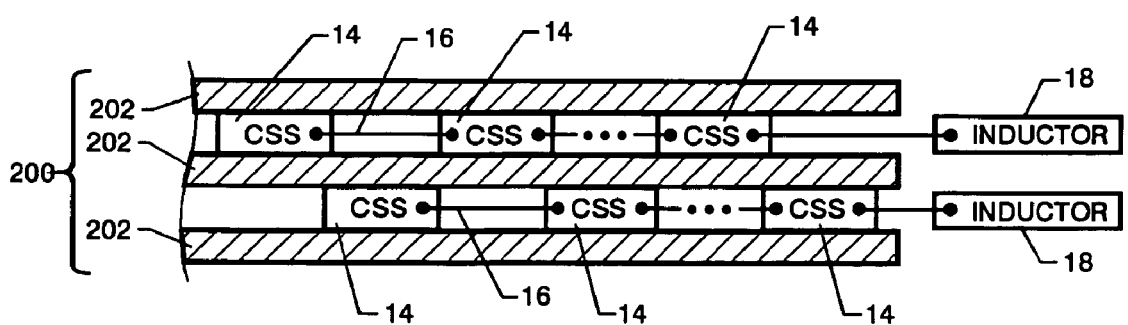
FIG. 4 is a side schematic view of a multi-layer structure having crack-sensing circuits disposed between the structure's layers.

The present invention can also be used to detect cracks in layers of a multi-layer structure. For example, as shown in FIG. 4, the connected ones of CSS 14 forming one of the above-described circuit arrangements can be positioned/interposed between layers 202 of a multi-layer structure 200. Thus, the present invention can be used to provide a three-dimensional "view" of crack detection and localization.

Figure 5:
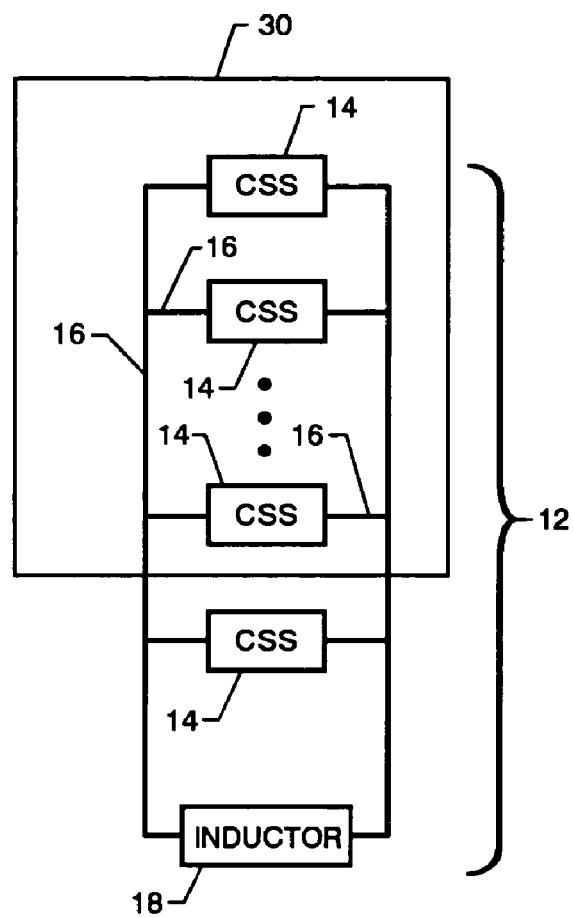
FIG. 5 is a schematic view of another crack-sensing circuit embodiment that includes a substrate.
Figure 6:
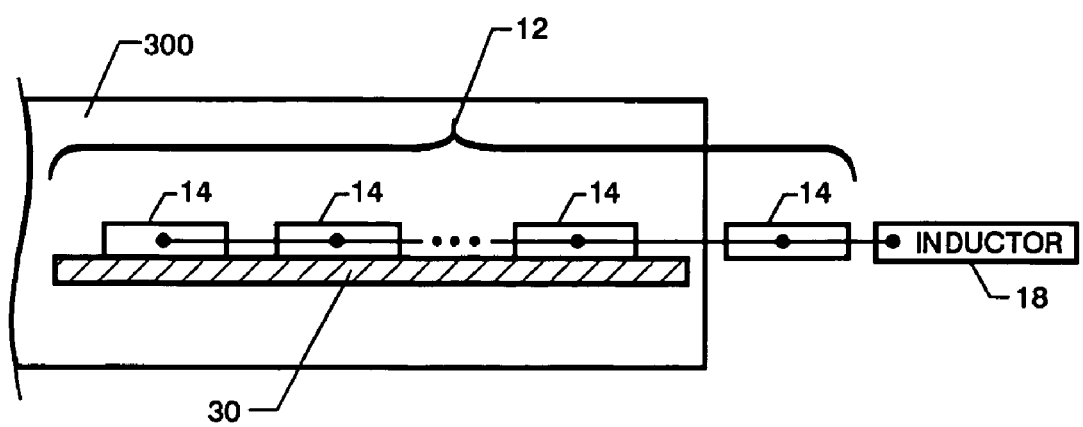
FIG. 6 is a side schematic view of the FIG. 5 crack-sensing circuit embodiment immersed in a curing material.

With reference now to FIGS. 5 and 6, the present invention can also be used to monitor crack formation during the curing process of a curable material or structure made from materials such as cement, resin, etc. In such a case, circuit arrangement 12 would typically be mounted on a substrate 30 such as a thin-film or mesh. Substrate 30 and circuit arrangement 12 would then be immersed in a material 300 prior to the curing thereof.

Figure 7:
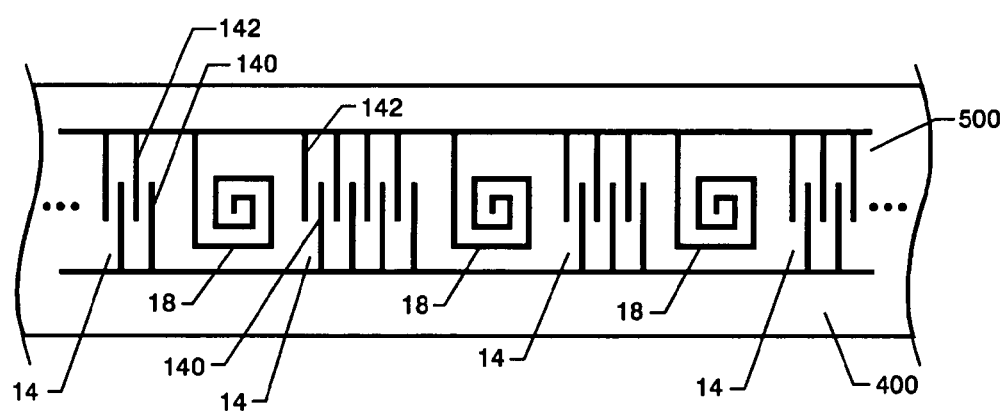
FIG. 7 is a schematic view of a crack-sensing circuit embodiment useful for package tampering detection.

Additionally, the present invention can be used to determine whether package tampering has occurred. Referencing FIG. 7, a repetition of inductors 18 and CSS 14 are electrically coupled in parallel, forming circuit 500, and deposited on a substrate 400 (e.g., tape with a low in-plane strength) that can be easily broken. Each CSS 14 can be constructed from sets of interdigitated electrodes 140/142. The circuit 500 should contain at least two inductors and three CSS 14 such that a CSS 14 is placed between the inductors and on either side of each inductor. The circuit 500 will thus result in one or more resonant circuits should the circuit 500 be broken anywhere on the circuit. The substrate 400 has an adhesive on at least one side for adherence to the surface (e.g., a package) to be monitored. The circuit 500 has a unique resonant frequency indicative of no damage/tampering. The resonant frequency is measured using a magnetic field response recorder 20 once the circuit 500 and substrate 400 are affixed on or in a package. Should tampering occur, the substrate 400 will be broken, thus breaking the circuit 500 resulting in one or more new resonant frequencies. The new resonant frequencies are indicative of package tampering. Once placed on the surface to be monitored, the substrate 400 is monitored using the magnetic field response recorder 20 to ascertain if the resonant frequency has changed, thus indicating whether the circuit has been broken. Such monitoring can indicate, for example, whether package tampering has occurred.

The advantages of the present invention are numerous. Cracks are detected and localized by a simple, in-situ system. Crack detection can be continuously or periodically monitored as needed. The system and method utilizes thin-film devices so that structure integrity and performance are not affected.

Although the invention has been described relative to a specific embodiment thereof, there are numerous variations and modifications that will be readily apparent to those skilled in the art in light of the above teachings. It is therefore to be understood that, within the scope of the appended claims, the invention may be practiced other than as specifically described.

What is claimed as new and desired to be secured by Letters Patent of the United States is:

1. A system for detecting cracks and their location in a structure, comprising:
   at least one circuit coupled to a structure, each said circuit having a plurality of capacitive strain sensors coupled sequentially and in parallel to one another wherein, when excited by a variable magnetic field, said circuit has a resonant frequency that is (i) a first resonant frequency when said circuit is in an unstrained state, (ii) one of a plurality of second resonant frequencies when said circuit is in a strained state, (iii) a third resonant frequency when said circuit has been broken and the remaining active circuit is in an unstrained state, said third resonant frequency being substantially different in frequency from said first resonant frequency, and (iv) one of a plurality of fourth resonant frequencies when said circuit is broken and the remaining active circuit is in a strained state, said fourth resonant frequencies being substantially different in frequency from said plurality of second resonant frequencies, each of said plurality of second resonant frequencies being indicative of a region of said circuit that is experiencing strain induced by strain in a region of the structure in proximity to said region of said circuit, said third resonant frequency being indicative of a region of said circuit that is broken, and each of said fourth resonant frequencies being indicative of a region of said remaining active circuit that is strained;

an inductor electrically coupled to one end of each said circuit; and a magnetic field response recorder for wirelessly transmitting said variable magnetic field to said inductor and for sensing said resonant frequency of said circuit so-excited by said variable magnetic field.

2. A system as in claim 1 wherein each of said capacitive strain sensors comprises interdigitated electrodes.

3. A system as in claim 1 wherein said structure is made from a homogenous material, and wherein said circuit is coupled to a surface of the homogenous material.

4. A system as in claim 1 wherein said structure is made from layers of material, and wherein said at least one circuit comprises a plurality of said circuits interposed between said layers.

5. A system as in claim 1 where said structure is made from an electrically non-conductive material, and wherein said circuit comprises thin-film metal conductors deposited directly on the structure.

6. A system as in claim 1 wherein said structure is made from an electrically conductive material, and wherein said circuit comprises:
    a thin-film electrical insulator deposited directly on said structure; and
    thin-film metal conductors deposited directly on said thin-film electrical insulator.

7. A system as in claim 1 wherein said structure is made from a curable material that is in the process of curing, and wherein said circuit is immersed in the curable material and comprises:
    a substrate; and
    thin-film metal conductors deposited directly on said substrate.

8. A system for detecting cracks and their location in a structure, comprising:
    at least one circuit partially coupled to a structure, each said circuit having N capacitive strain sensors coupled sequentially and in parallel to one another with a first through (N–1) capacitive stain sensors coupled to the structure and an N-th capacitive strain sensor being uncoupled from the structure wherein, when excited by a variable magnetic field, said circuit has a resonant frequency that is (i) a first resonant frequency when said circuit is in an unstrained state, (ii) one of a plurality of second resonant frequencies when said circuit is in a strained state, (iii) a third resonant frequency when said circuit has been broken and the remaining active circuit is in an unstrained state, said third resonant frequency being substantially different in frequency from said first resonant frequency, and (iv) one of a plurality of fourth resonant frequencies when said circuit is broken and the remaining active circuit is in a strained state, said fourth resonant frequencies being substantially different in frequency from said plurality of second resonant frequencies, each of said plurality of second resonant frequencies being indicative of a region of said circuit that is experiencing strain induced by strain in a region of the structure in proximity to said region of said circuit, said third resonant frequency being indicative of a region of said circuit that is broken, and each of said fourth resonant frequencies being indicative of a region of said remaining active circuit that is strained;

an inductor electrically coupled to one end of each said circuit via said N-th capacitive strain sensor associated therewith; and a magnetic field response recorder for wirelessly transmitting said variable magnetic field to said inductor and for sensing said resonant frequency of said circuit so-excited by said variable magnetic field.

9. A system as in claim 8 wherein each of said N capacitive strain sensors comprises interdigitated electrodes.

10. A system as in claim 8 wherein said structure is made from a homogenous material, and wherein said first through (N–1) capacitive stain sensors are coupled to a surface of said homogenous material.

11. A system as in claim 8 wherein said structure is made from layers of material, and wherein said at least one circuit comprises a plurality of said circuits interposed between said layers.

12. A system as in claim 8 wherein said structure is made from an electrically non-conductive material, and wherein said first through (N–1) capacitive stain sensors comprises thin-film metal conductors deposited directly on the structure.

13. A system as in claim 8 wherein said structure is made from an electrically conductive material, and wherein said first through (N–1) capacitive stain sensors comprise:
    a thin-film electrical insulator deposited directly on said structure; and
    thin-film metal conductors deposited directly on said thin-film electrical insulator.

14. A system as in claim 8 where said structure is made from a curable material that is in the process of curing, and wherein said first through (N–1) capacitive stain sensors are immersed in the curable material.

15. A method of detecting cracks and their location in a structure, comprising the steps of:
    providing a circuit that includes a plurality of capacitive strain sensors coupled sequentially and in parallel to one another;
    coupling at least a portion of said circuit to a structure;
    coupling an inductor to one end of said circuit;
    inducing a variable magnetic field in said inductor wherein, when excited by said variable magnetic field, said circuit has a resonant frequency that is (i) a first resonant frequency when said circuit is in an unstrained state, (ii) one of a plurality of second resonant frequencies when said circuit is in a strained state, (iii) a third resonant frequency when said circuit has been broken and the remaining active circuit is in an unstrained state, said third resonant frequency being substantially different in frequency from said first resonant frequency, and (iv) one of a plurality of fourth resonant frequencies when said circuit is broken and the remaining active circuit is in a strained state, said fourth resonant frequencies being substantially different in frequency from said plurality of second resonant frequencies, each of said plurality of second resonant frequencies being indicative of a region of said circuit that is experiencing strain induced by strain in a region of the structure in proximity to said region of said circuit, said third resonant frequency being indicative of a region of said circuit that is broken, and each of said fourth resonant frequencies being indicative of a region of said remaining active circuit that is strained; and sensing said resonant frequency of said circuit so-excited by said variable magnetic field.

16. A method according to claim 15 wherein said structure is made from a homogenous material, and wherein said circuit is coupled to a surface of said homogenous material.

17. A method according to claim 15 wherein said structure is made from layers of material, and wherein said circuit is interposed between two of the layers.

18. A method according to claim 15 where said structure is made from an electrically non-conductive material, and wherein said step of coupling said circuit to the structure comprises the step of depositing thin-film metal conductors directly on the structure.

19. A method according to claim 15 wherein said structure is made from an electrically conductive material, and wherein said step of coupling said circuit to the structure comprises the steps of:
   depositing a thin-film electrical insulator directly on said structure; and
   depositing thin-film metal conductors directly on said thin-film electrical insulator.

20. A method according to claim 15 wherein said structure is made from a curable material that is in the process of curing, and wherein said step of coupling said circuit to said structure comprises the step of immersing said circuit in said curable material.

21. A system for detecting cracks and their location in a structure, comprising:
   at least one circuit coupled to a structure, each said circuit having at least three capacitive strain sensors wherein, when excited by a variable magnetic field, said circuit has a resonant frequency that is (i) a first resonant frequency when said circuit is in an unbroken state, and (ii) one of a plurality of second resonant frequencies when said circuit is in a broken state, each of said plurality of second resonant frequencies being indicative of a region of said circuit that is broken;
   at least two inductors electrically coupled to each said capacitive strain sensor, wherein each inductor is positioned between two capacitive strain sensors; and
   a magnetic field response recorder for wirelessly transmitting said variable magnetic field to said one or more inductors and for sensing said resonant frequency of said circuit so-excited by said variable magnetic field.

22. A system as in claim 21 wherein each of said capacitive strain sensors comprises interdigitated electrodes.

23. A system as in claim 21 wherein said circuit is deposited on a substrate affixed to the structure.

24. A system as in claim 23 wherein said substrate can be easily broken.

25. A system as in claim 23 wherein said substrate is tape having a low in-plane strength.

26. A system as in claim 24 wherein said breaking of said substrate is indicative of tampering with said structure.

27. A method of detecting product tampering, comprising the steps of:
   providing a circuit that comprises at least three capacitive strain sensors;
   coupling at least a portion of said circuit to a structure;
   coupling at least two inductors to each capacitive strain sensor, wherein each inductor is positioned between two capacitive strain sensors;
   inducing a variable magnetic field in each inductor wherein, when excited by said variable magnetic field, said circuit has a resonant frequency that is (i) a first resonant frequency when said circuit is in an unstrained state, and (ii) one of a plurality of second resonant frequencies when said circuit is in a strained state, each of said plurality of second resonant frequencies being indicative of a region of said circuit that is experiencing strain induced by strain in a region of the structure in proximity to said region of said circuit; and
   sensing said resonant frequency of said circuit so-excited by said variable magnetic field.

28. A system as in claim 27 wherein said circuit is deposited on a substrate affixed to the structure.

29. A system as in claim 28 wherein said substrate can be easily broken.

30. A system as in claim 29 wherein said substrate is tape having a low in-plane strength.

31. A system as in claim 29 wherein said breaking of said substrate is indicative of tampering with said structure.

* * * * *